(12) United States Patent
Farquharson et al.

(10) Patent No.: US 9,028,560 B2
(45) Date of Patent: May 12, 2015

(54) ARTIFICIAL ARM PROSTHESIS TERMINAL DEVICE

(71) Applicants: Ronald H. Farquharson, Brazoria, TX (US); Johnnie Rouse, Angleton, TX (US)

(72) Inventors: Ronald H. Farquharson, Brazoria, TX (US); Johnnie Rouse, Angleton, TX (US)

(*) Notice: Subject to any disclaimer, the term of this patent is extended or adjusted under 35 U.S.C. 154(b) by 0 days.

(21) Appl. No.: 14/481,409

(22) Filed: Sep. 9, 2014

(65) Prior Publication Data

US 2015/0012114 A1    Jan. 8, 2015

(51) Int. Cl.
*A61F 2/54* (2006.01)
*A61F 2/58* (2006.01)

(52) U.S. Cl.
CPC .. *A61F 2/54* (2013.01); *A61F 2/588* (2013.01)

(58) Field of Classification Search
CPC .............. A61F 2/54; A61F 2/58; A61F 2/588
USPC .............................. 623/61, 62, 65; 279/74–76
See application file for complete search history.

(56) References Cited

U.S. PATENT DOCUMENTS

| | | | |
|---|---|---|---|
| 3,490,078 A | 1/1970 | Perez | |
| 3,802,302 A | 4/1974 | Bengtson | |
| 3,942,194 A | 3/1976 | Winter | |
| 4,661,113 A | 4/1987 | Adkins | |
| 4,944,765 A | 7/1990 | Keith | |
| 5,163,966 A | 11/1992 | Norton et al. | |
| 5,464,444 A | 11/1995 | Farquharson et al. | |
| 5,573,255 A * | 11/1996 | Salpaka | 279/75 |
| 8,795,387 B1 * | 8/2014 | Razink | 623/62 |
| 2007/0260328 A1 * | 11/2007 | Bertels et al. | 623/38 |
| 2013/0186491 A1 * | 7/2013 | Liu | 137/614 |

* cited by examiner

*Primary Examiner* — Bruce E Snow
(74) *Attorney, Agent, or Firm* — Law Office of Stephen P. Krupp, PLLC

(57) ABSTRACT

A terminal device is described which is attachable to the end of a prosthesis on an arm and there serves as an attachment site for a variety of tools or implements designed to mate with the terminal device. A locking ring mechanism is also described herein. The terminal device comprises a first main part in operable and pivotal combination with a second main part, the combined main parts providing on one end a device for attaching to the end of an a prosthesis, and on the other a device for attaching a variety of implements, the said device for implement attachment providing articulation capabilities that allow positioning of the implements in a variety of positions relative to the position of the arm prosthesis. Among the implements which can be attached are for example: cutting tools (such as saws, files, knives, scrapers, and awls); various wrenches (such as open end wrenches, closed end wrenches, ratchet wrenches, adjustable wrenches, Allen wrenches, and pipe wrenches); and a variety of other implements such as spoons, scoops, spatulas, planes, brushes, sports equipment (e.g., fishing rods), and stirring devices.

10 Claims, 9 Drawing Sheets

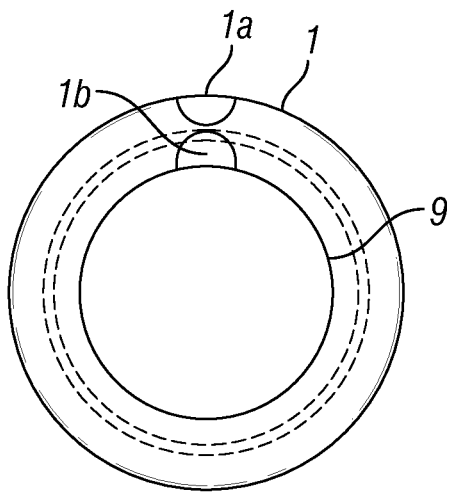
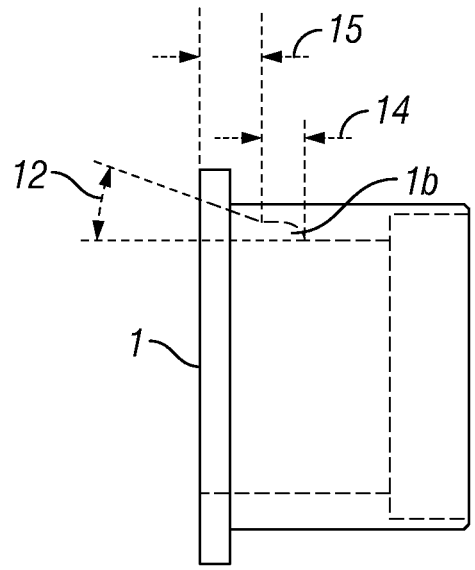
FIG. 7A  FIG. 7B
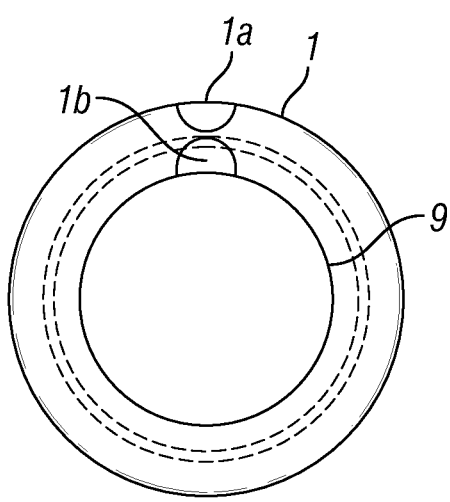
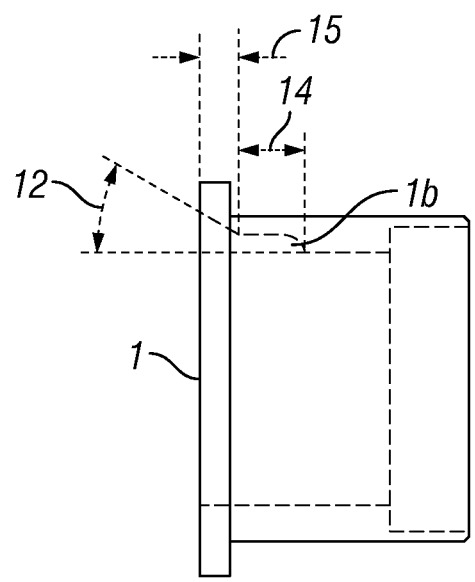
FIG. 8A  FIG. 8B

ARTIFICIAL ARM PROSTHESIS TERMINAL DEVICE

FIELD OF THE INVENTION

Attachment for an artificial arm prosthesis providing connection thereto with a variety of connectable implements.

BACKGROUND OF THE INVENTION

There have been a number of prosthetic devices for use by amputees who have lost at least one or both hands, or one or both arms or debilitating hand dysfunction. Many of the devices are body powered and some are driven, or at least assisted, by electrical, myoelectrical, and/or pneumatic means. Many of the sophisticated devices are very expensive to manufacture and repair.

There are commonly used devices which attach to a prosthesis fastened to the remaining part of an arm on which a hand is missing and in which the device (sometimes called a "cup" or "cuff") at the distal end is designed to accept certain tools that are mechanically, but removably, attached to the cup. Such "cups" or "cuffs" can be an attachment position at the distal end of an expensive, complex prosthesis, or a relatively inexpensive, simple prosthesis or wrist hand orthosis ("WHO"), Various U.S. Patents disclose different devices.

U.S. Pat. No. 3,490,078 (Perez) discloses a flexible sleeve for a forearm stump which has a threaded female member at the end of the sleeve into which can be threaded a handle of a tool.

U.S. Pat. No. 3,802,302 (Bengtson) discloses a tool holding prosthetic device having a threaded connector devices for attaching various tools and shows the use of a detent ball.

U.S. Pat. No. 3,942,194 (Winter) discloses a device for attaching to a hand to which an implement can be removably fastened U.S. Pat. No. 4,661,113 (Adkins) discloses a device which is attachable to an amputee's prosthesis to enable the amputee to swing a golf dub or other device which requires swinging.

U.S. Pat. No. 5,163,966 (Norton et al) discloses a prosthetic limb having a means for grasping and holding a bar or tubular member.

U.S. Pat. No. 4,944,765 (Keith) discloses an artificial arm prosthetic drive device for holding a rotatable tool.

U.S. Pat. No. 5,464,444 (Farquharson et al.) discloses an attachment for an arm prosthetic device.

In High Tech for The Handicapped by Larry Kettelkamp, published by Enslow Publishers, Inc. Hillside, N.J., 1991, there is described a prosthesis called the "Utah Arm", shown in exploded view, which illustrates a wrist rotator which has annular threads for receiving the threaded extension of gripping devices or artificial hand that is interchangeable and operates on a battery pack.

There is a perceived need for ways and means that permit the wearer of an arm prosthesis to have enhanced capabilities in the type and operation of mechanically attached implements.

The present invention is directed principally to providing for mechanical attachments of implements to prosthetic devices which are adaptable for movement by the wearer, using mechanical, pneumatic, electrical or electromechanical movement of implements removably affixed to the end of an arm. Specifically, the invention provides for a rotational and axial locking mechanism for such devices. The locking mechanism is also useful for devices other than prosthetic devices.

Throughout this disclosure the expression "terminal device" is used in the ordinary vernacular of arm prostheses as a device added to an arm prosthesis at a wrist location. The terms "tool connector" and "tool coupler" refer to parts which are used for coupling the tool with the terminal device. "Tool" and "implement" each refer to the item being coupled with the terminal device.

SUMMARY OF THE INVENTION

One aspect of the invention is a terminal device for releasable attachment to the distal end of an arm prosthesis and providing means for coupling with an implement in a variety of positions relative to the arm prosthesis, said terminal device comprising a structure having a proximate end chassis base and an distal end locking collar, said chassis base attached to the distal end of the prosthesis, and said locking collar being operably, preferably threadably, affixed onto an articulating clevis pivotably and perpendicularly mated into a slotted opening traversing the chassis base, the distal end locking collar of the having a hollow end for releasable insertion therein of an implement by means of an implement coupling part comprising a locking ring mechanism, wherein the locking ring mechanism comprises a locking ring, a locking ball, a locking spring, and a tool socket, wherein the locking ring comprises a visual locking ball locating indent, a locking ball groove comprising an angled section length and a straight section length, the angled section length located on the locking ring implement connecting end and comprising at least about 10% of the straight section length, the locking ball groove in close proximity to the visual locking ball locating indent;

a locking ball constrained within a locking ball hole in the tool socket and in communication with the locking ball groove;

wherein the tool socket comprising the locking ball is concentrically surrounded by the locking spring, which locking spring is in turn concentrically surrounded by the locking ring, wherein the pivotable means is provided by a lead screw mounted within, and traversing, the chassis base in a direction parallel to the fore-aft axial alignment thereof, and mounted within, and traversing, the articulating clevis in a direction normal to the distal-proximate axial alignment thereof, said lead screw communicating with lead screw nut of said articulating clevis, said lead screw being revolvable by means visibly mounted, preferably by means of a lead screw cap ball, at one end of said lead screw.

Preferably, the angled section length has an angle greater than 5 degrees and as high as 50 degrees, more preferably greater than 10 degrees and up to 50 degrees, especially from about 15 degrees to about 30 degrees. Separately or in combination with these angles, the angled section length located on the locking ring implement connecting end can comprise from at least about 10% of the straight section length to 100% of the straight section length.

The chassis base can have a threaded extension on its proximal end for threading into an annular threaded receptacle adapter of matching size and threads, said receptacle being at the distal end of an arm prosthesis. In a related embodiment, a cable stay attachment is attached to the articulating clevis and into the chassis base of the terminal device.

Preferably, the implement coupling part comprises a circular bar of a dimension to fit closely within the hollow portion of the distal end of the locking collar of the terminal device, said implement coupling part having at least one securing detent and/or a securing groove operable at its outer surface which cooperates in releasable connection with a locking ball within said hollow portion when the implement coupling part is inserted into said hollow portion.

The implement held by the implement coupling part is preferably selected from groups consisting of cutting tools, wrenches, clamping tools, screw drivers, hammers, scrapers, brushes, pencils, awls, scoops, planes, fishing rods, and stirring devices.

Preferably, at least the articulating clevis and the chassis base of the terminal device are constructed of aircraft aluminum alloy.

The terminal device can further comprise a tool or implement radially and axially attached to the locking ring by means of at least one detent.

Another aspect of the invention is a locking ring mechanism comprising a locking ring, a least one locking ball, a locking spring, and a tool socket, wherein the locking ring comprises an internal locking ball groove comprising an angled section length and a straight section length, the angled section length located on the locking ring implement connecting end and comprising at least about 10% of the straight section length; a locking ball constrained within a locking ball hole in the tool socket and in communication with the locking ball groove; wherein the tool socket comprising the locking ball is concentrically surrounded by the locking spring, which locking spring is in turn concentrically surrounded by the locking ring.

Preferably, the angled section length of the locking ring mechanism located on the locking ring implement has an angle greater than 5 degrees and as high as 50 degrees, more preferably greater than 10 degrees and up to 50 degrees, and especially from about 115 degrees to about 30 degrees. Separately or in combination with these angles, the angled section length located on the locking ring implement connecting end can comprise from at least about 10% of the straight section length to 200% of the straight section length. Further, the straight section length located on the locking ring implement connecting end preferably comprises at least 50% of a diameter of the at least one locking ball.

In another embodiment of this second aspect of the invention, the locking ring mechanism can further comprise a tool or implement radially and axially attached to the locking ring by means of at least one detent.

BRIEF DESCRIPTION OF THE DRAWINGS

FIGS. 1-13, not drawn to any particular scale, are presented as visual aids in relating embodiments the invention.

FIG. 1 illustrates a perspective view of a terminal device.

FIG. 2 illustrates a mirrored view of FIG. 1 (the device turned end for end in the horizontal axis).

FIG. 3 is an end-on view of the terminal device looking down the locking collar 1 and showing the optional cable stay 13 showing cable stay attachment ring 13a at its exterior end, FIG. 4 is a plan view of the terminal device, which is shown in a different plan view in FIG. 1, showing the optional cable stay 13 protruding from the articulating clevis FIG. 5 is a mirror view of FIG. 4, barely showing the lead screw cap ball 5 on the back side of the figure, but prominently showing lead screw end 10.

FIG. 6A shows locking collar 1 end-on which concentrically surrounds tool socket 9. FIG. 6B shows a side cross section view of locking collar 1, showing locking ball groove 1b having an exit angle 12.

FIG. 7A and FIG. 7B show two perspectives of locking collar 1. FIG. 7A shows locking ring 1 end-on which concentrically surrounds tool socket 9. FIG. 7B shows a side cross section view locking collar 1, showing locking ball groove 1b having an exit angle 12.

FIG. 8A and FIG. 8B show two perspectives of locking collar 1. FIG. 8A shows locking collar 1 end-on which concentrically surrounds tool socket 9. FIG. 8B shows a side cross section view of locking collar 1, showing locking ball groove 1b having an exit angle 12.

FIG. 9A shows open channel 2b facing the viewer, with pivot screw or optional cable stay receiving hole 2c and threaded portion 2a (which threads into tool socket 9 (not shown in FIGS. 9A and 9B)). FIG. 9B shows the articulating clevis 2 turned 90 degrees, with the open channel 2b now in the vertical position.

FIG. 10A shows open channel 2b facing the viewer, lead screw receiving hole 3d, with pivot screw or optional cable stay receiving hole 3c and threaded portion 3a (which threads into an arm prosthetic socket (not shown). FIG. 10B shows the chassis base 3 turned 90 degrees, with the open channel 3b now in the vertical position.

FIG. 11 shows an exploded view of locking collar 1, locking spring 7, tool socket 9 having locking ball hole 9a, articulating clevis 2 and chassis base 3, in the preferred order of assembly, from left to right.

FIGS. 12 and 13 are duplicate figures of FIGS. 1 and 2, respectively, but not showing the optional cable stay 13.

FIG. 16 shows the placement of the locking ball 8 various depths and spatial relationships to other components of locking collar 1.

DETAILED DESCRIPTION

A terminal device is described which is attachable to the end of an arm prosthesis which serves as an attachment site for a variety of tools or implements designed to mate with the device. The device comprises a main part which has on one end a means for attachment to the end of an arm prosthesis, and on the other a means for attaching a variety of implements, the said means for implement attachment providing articulation capabilities that allow positioning the implements in a variety of positions relative to the position of the arm prosthesis. Among the implements which can be attached are for example: cutting tools (such as saws, files, knives, scrapers, and awls); various wrenches (such as open end wrenches, closed end (or box) wrenches, ratchet wrenches, adjustable wrenches, Allen wrenches, and pipe wrenches); and a variety of other implements such as brushes, fishing rods, sporting devices in general, spoons, scoops, spatulas, planes, and stirring devices.

Figure 1:
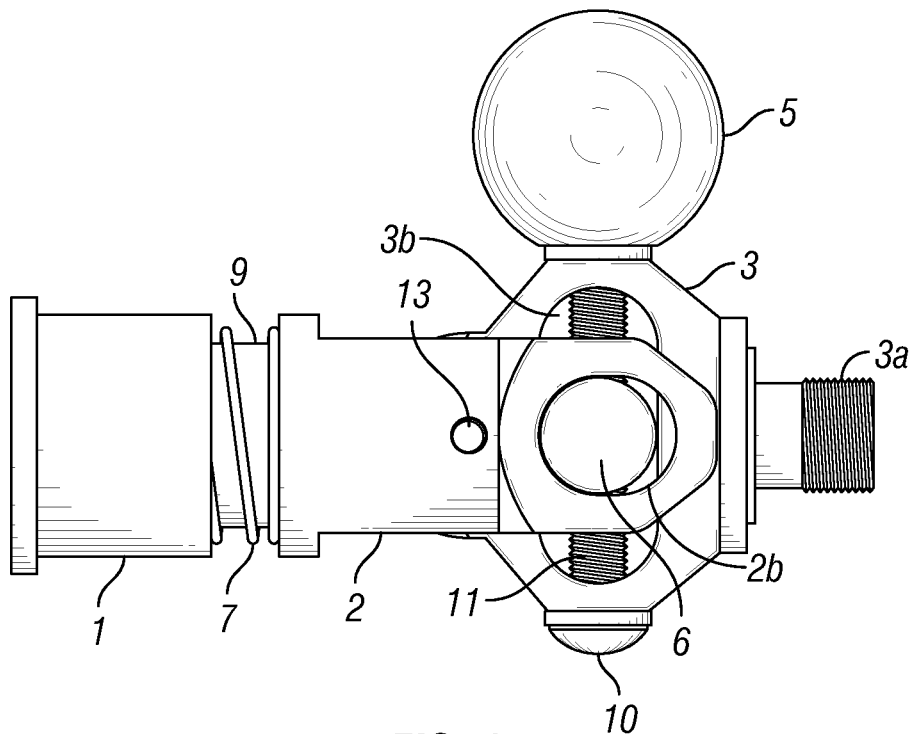

Further descriptions of the invention and of the drawings are presented below:

FIG. 1 illustrates a perspective view of a terminal device having a chassis base 3, which has a threaded end 3a, an open channel portion 3b, a lead screw receiving hole 3c (shown in FIGS. 10A and 10B), and a pivot screw or cable stay receiving hole 3d (shown in FIGS. 10A and 10B) combined with an articulating clevis 2, which has a threaded portion 2a (shown in FIGS. 9A and 9B), an open channel portion 2b and a pivot screw or cable stay receiving hole 2c (shown in FIGS. 9A and 9B), a tool socket 9, a locking spring 7 and a locking collar 1 (sometimes called a quick disconnect fitting ring). Lead screw ball 5 is connected to the lead screw 11. Lead screw 11 is passed through the open channel portion of the chassis base 3b and the open channel portion 2b of the articulating clevis 2, and threaded through the lead screw nut 6. Lead screw nut 6 is inserted parallel into the channel portion 2b of the articulating clevis 2 and perpendicularly into the channel portion 3b of the chassis base 3.

Figure 2:
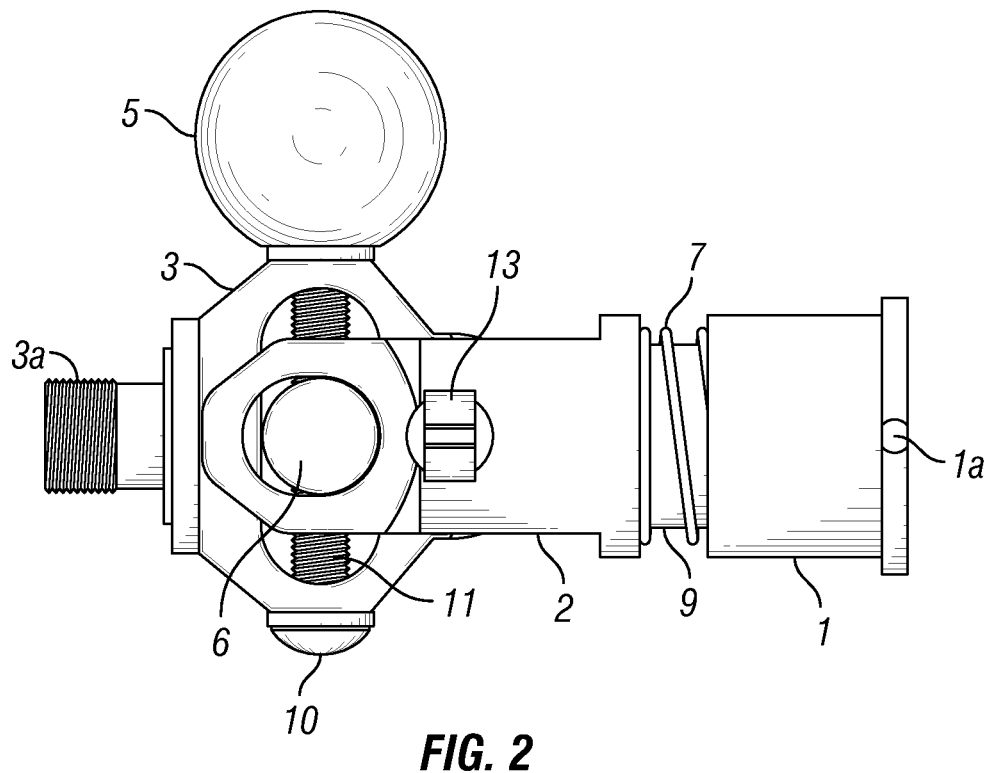

FIG. 2 illustrates a mirrored view of FIG. 1 (the device turned end for end in the horizontal axis).

Figure 3:
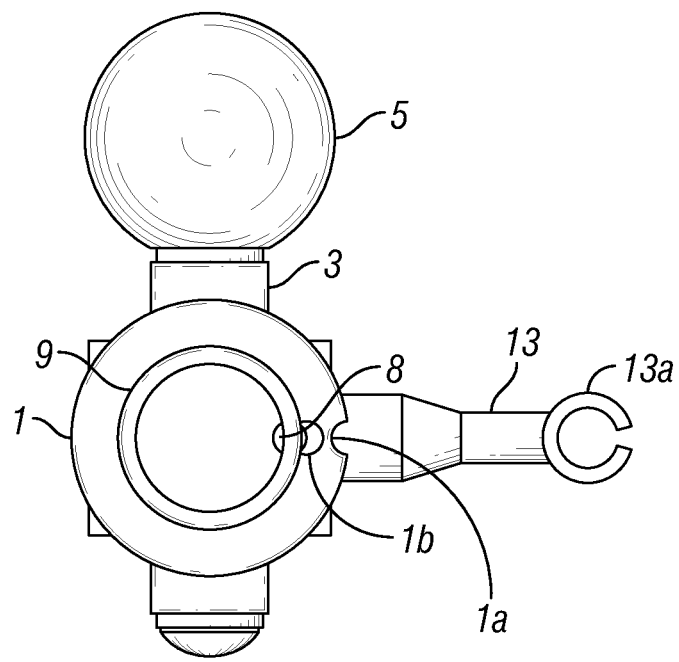

FIG. 3 is an end-on view of the device looking down the locking ring 1 and showing the optional cable stay 13 showing cable stay attachment ring 13a at its exterior end. Locking collar indent 1a is shown, as is locking ball groove 1b. Locking ball 8 is shown sitting in locking ball groove 1b and contained by tool socket locking ball hole 9a (not shown in FIG. 3, but shown in FIG. 11).

Figure 4:
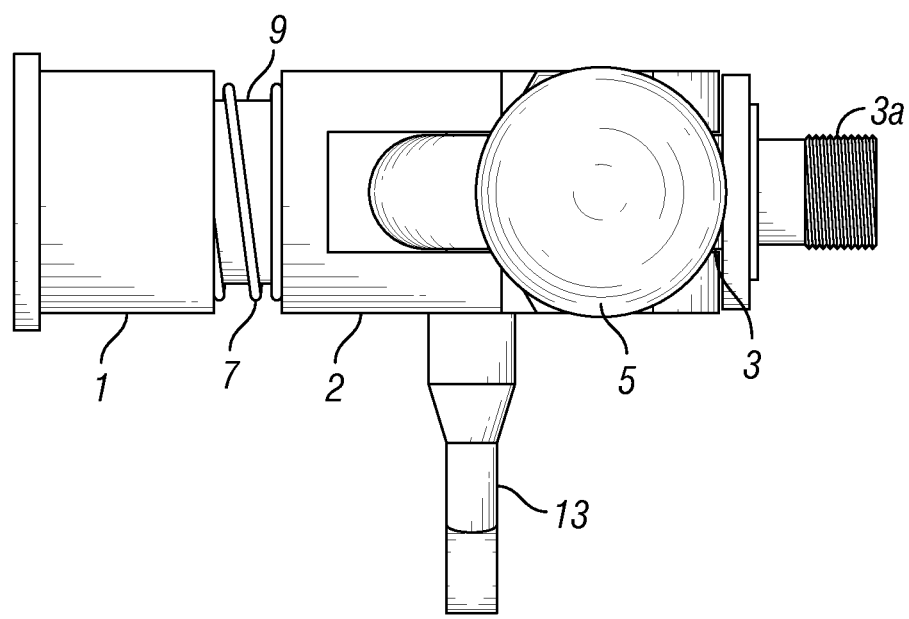

FIG. 4 is a plan view of the terminal device, which is shown in a different plan view in FIG. 1, showing the optional cable stay 13 protruding from the articulating clevis 2.

Figure 5:
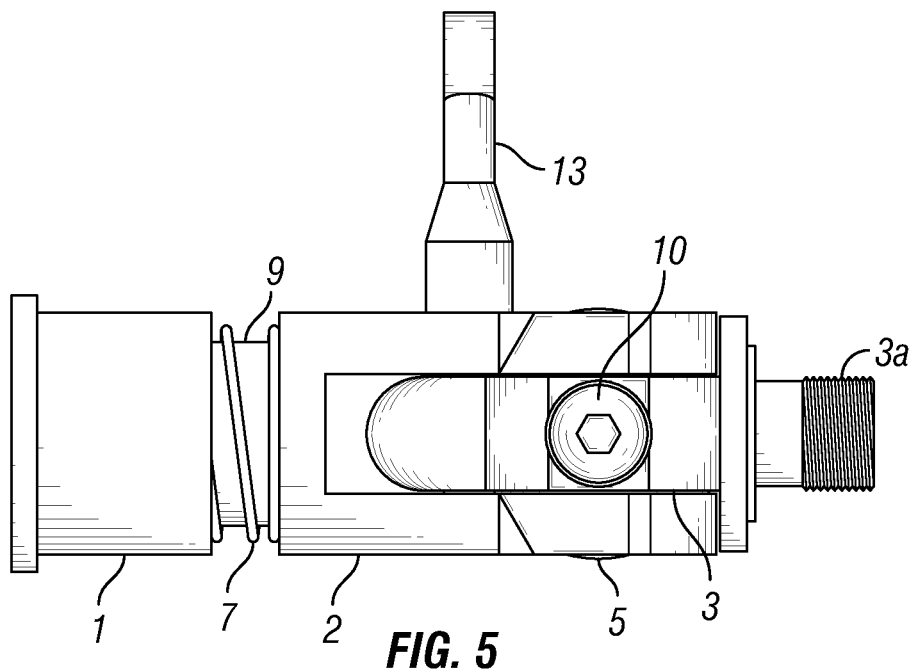

FIG. 5 is a mirror view of FIG. 4, barely showing the lead screw cap ball 5 on the back side of the figure, but prominently showing lead screw end 10.

Figure 6A:
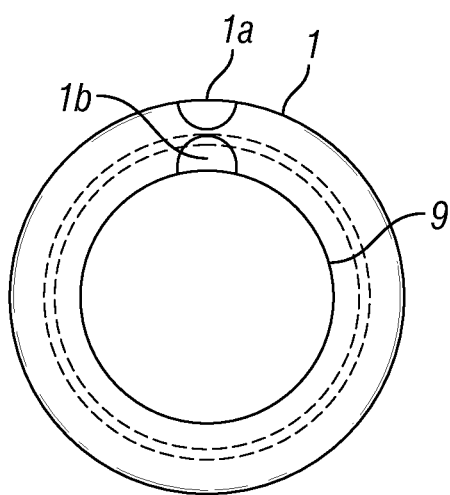
FIG. 6A and FIG. 6B show two perspectives of locking collar 1.
Figure 6B:
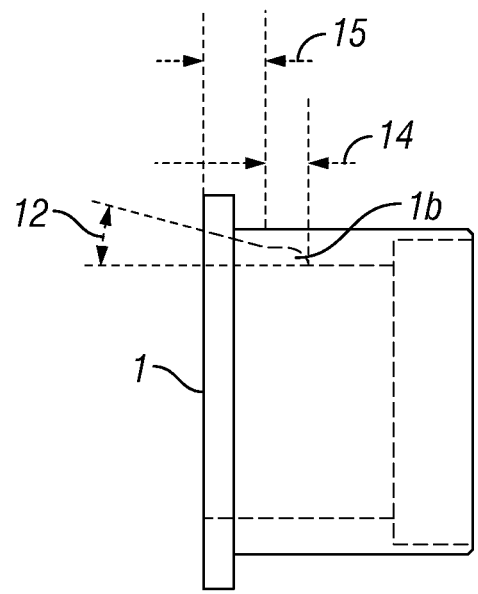

FIG. 6 A and FIG. 6B show two perspectives of locking collar 1 (the locking ring collar implement connecting end). FIG. 6A shows locking collar 1 end-on which concentrically surrounds tool socket 9. FIG. 6B shows a side cross section view of locking collar 1, showing locking ball groove 1b having an exit angle 12. In FIG. 6B, exit angle 12 is 15 degrees and straight section 14 is about 0.18 inches.

FIG. 7A and FIG. 7B show two perspectives of locking collar 1 (the locking ring collar implement connecting end). FIG. 7A shows locking collar 1 end-on which concentrically surrounds tool socket 9. FIG. 7B shows a side cross section view of locking collar 1, showing locking ball groove 1b having an exit angle 12. In FIG. 7B, exit angle 12 is 20 degrees and straight section 14 is about 0.18 inches.

Figure 9A:
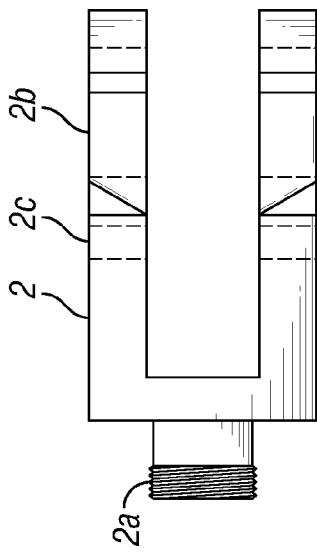
FIGS. 9A and 9B shows two perspectives of articulating clevis 2.
Figure 9B:
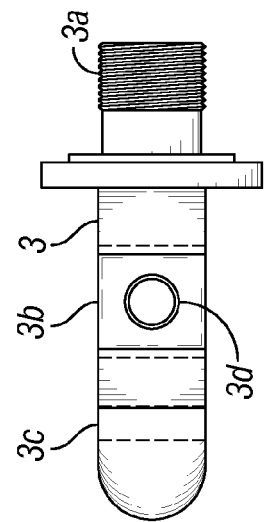

FIG. 8A and FIG. 8B show two perspectives of locking collar 1 (the locking ring collar implement connecting end). FIG. 8A shows locking collar 1 end-on which concentrically surrounds tool socket 9. FIG. 8B shows a side cross section view of locking collar 1, showing locking ball groove 1b having an exit 12. In FIG. 8B, exit angle 12 is 30 degrees and straight section 14 is about 0.2 inches, FIGS. 9A and 9B shows two perspectives of articulating clevis 2, FIG. 9A shows open channel 2h facing the viewer, with pivot screw or optional cable stay receiving hole 2c and threaded portion 2a (which threads into tool socket 9 (not shown in FIGS. 9A and 9B)). FIG. 9B shows the articulating clevis 2 turned 90 degrees, with the open channel 2b now in the vertical position.

Figure 10A:
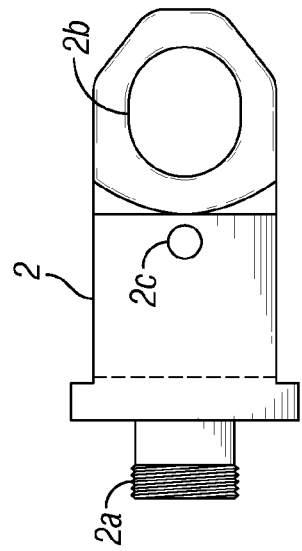
FIGS. 10A and 10B shows two perspectives of chassis base 3.
Figure 10B:
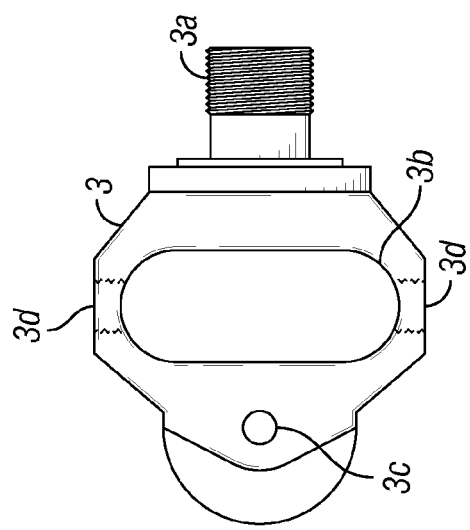

FIGS. 10A and 10B shows two perspectives of chassis base 3. FIG. 10A shows open channel 3b facing the viewer, lead screw receiving hole 3d, with pivot screw or optional cable stay receiving hole 3c and threaded portion 3a (which threads into an arm prosthetic socket (not shown). FIG. 10B shows the chassis base 3 turned 90 degrees, with the open channel 3b now in the vertical position.

Figure 11:
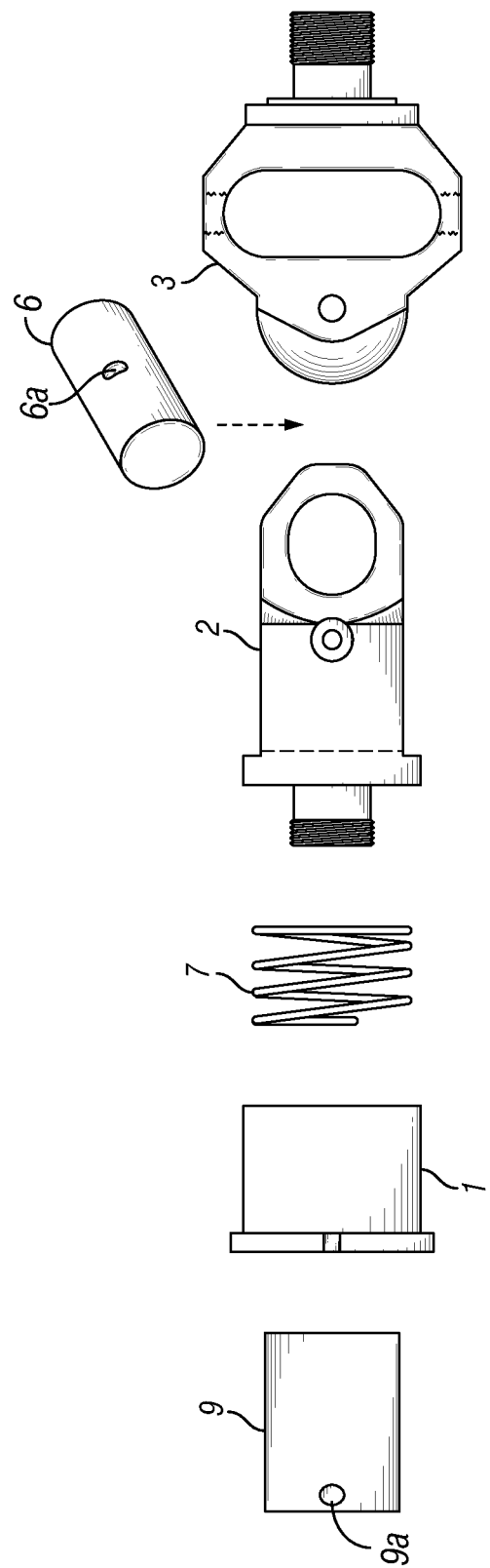

FIG. 11 shows an exploded view of locking collar 1, locking spring 7, tool socket 9 having locking ball hole 9a, articulating clevis 2 and chassis base 3, in the preferred order of assembly, from left to right. In this assembly, locking ball 8 is first inserted into the tool socket locking hole, the locking collar 1 is slipped over the tool socket, with locking spring 7 inside the locking collar 1 and around tool socket 9—this locking collar/locking ball/locking spring/tool socket assembly is then screwed onto the articulating clevis 2 by means of the male threaded portion 2a into the female threaded portion of the tool socket (not shown but inside the tool socket end opposite tool socket locking ball hole).

Figure 12:
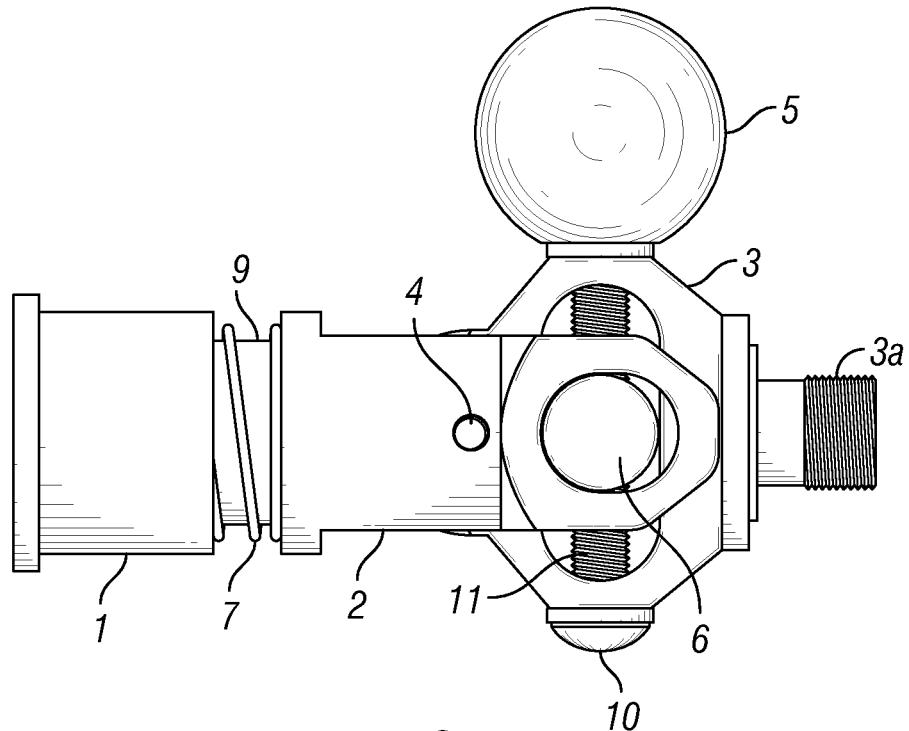
Figure 13:
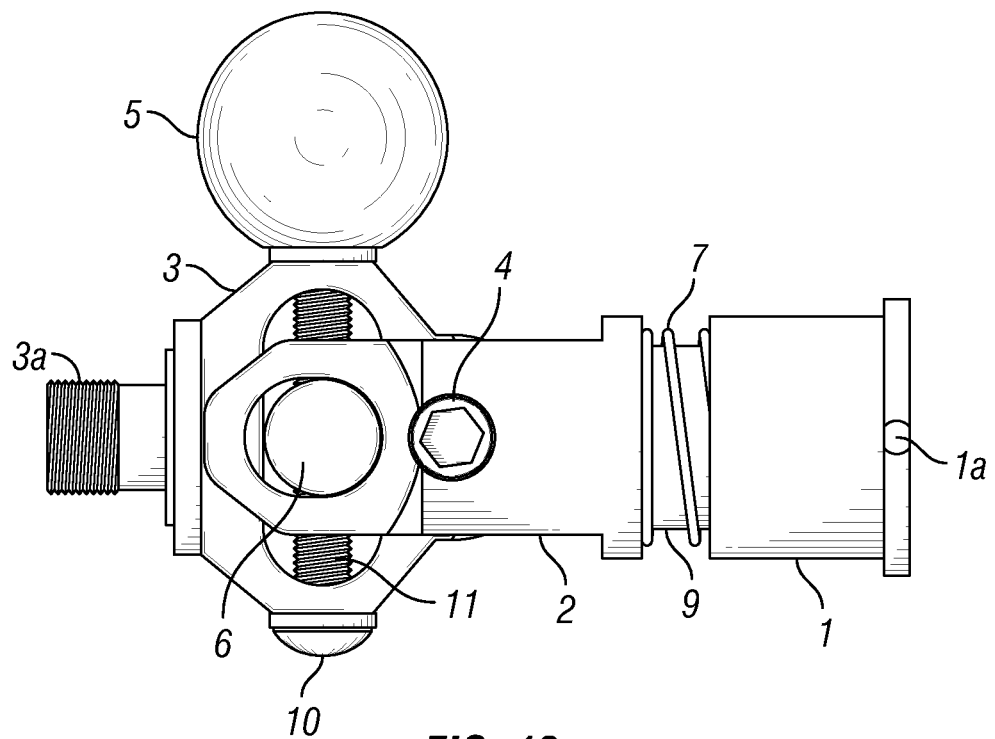

FIGS. 12 and 13 are duplicate figures of FIGS. 1 and 2, but not showing the optional cable stay 13. FIGS. 12 and 13 show the pivot screw 4 instead of the optional cable stay 13 depicted in FIGS. 1 and 2.

Figure 14:
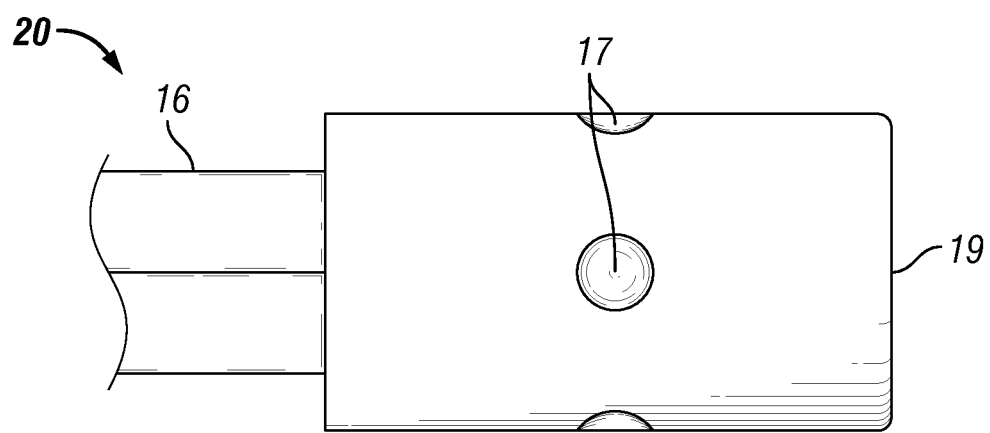
FIG. 14 depicts an overall tool or implement) 20 which can be attached to the device's locking collar at tool/implement end 19 using detents 17.

FIG. 14 depicts an overall tool (or implement coupling part) 20 which can be attached to the device's locking collar at tool/implement end 19. Tool/implement end 19 comprises the designed tool (e.g., a spoon, a knife, a fork) and detents 17 act to lock in the locking ball 8 contained in the locking collar shown in FIG. 3.

Figure 15:
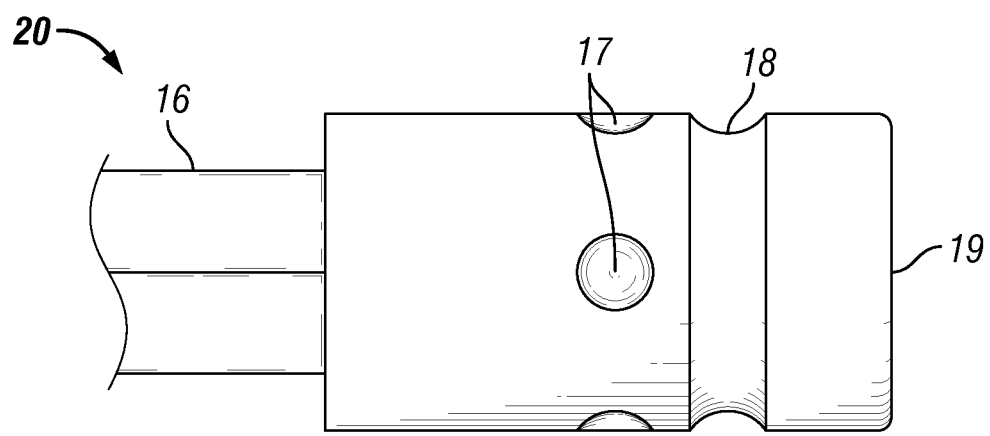
FIG. 15 depicts an overall tool (or implement) 20 which can be attached to the device's locking collar at tool/implement end 19 using detents 17 or groove.

FIG. 15 depicts an overall tool (or implement coupling part) 20 which can be attached to the device's locking collar at tool/implement end 19. Tool/implement end 19 comprises the designed tool (e.g., a spoon, a knife, a fork) and detents 17 act to lock in the locking ball 8 contained in the locking collar shown in FIG. 3. FIG. 15 also shows a groove 18 which allows the tool/implement to rotate about the axis of the device with locking ball 8 placed in the groove 18.

Figure 16:
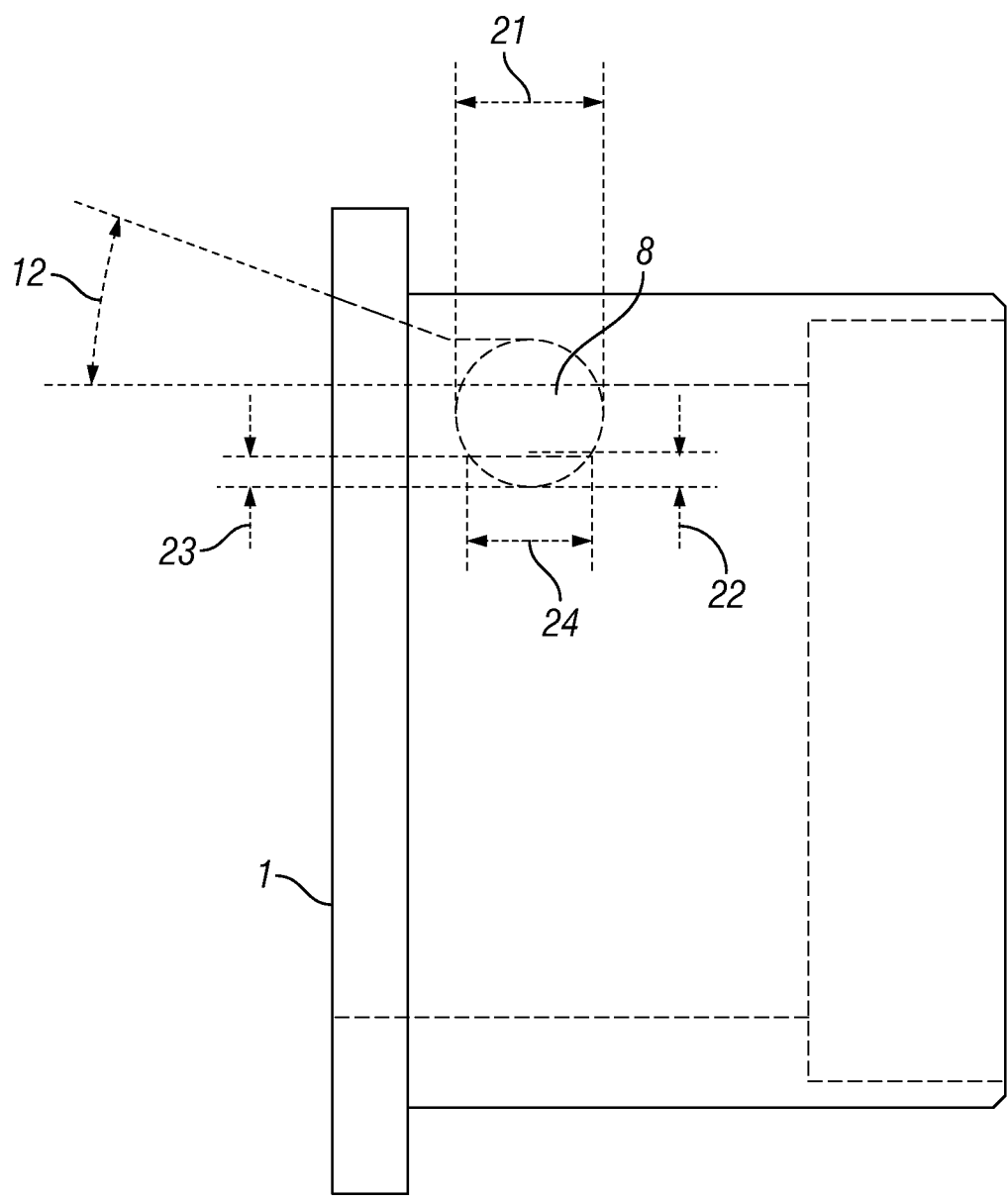
FIG. 16 shows locking collar 1 independent from other components of the device. In particular.

FIG. 16 shows locking collar 1 independent from other components of the device. In particular, FIG. 16 shows the placement of the locking ball 8 and Locking Ball Engagement Depth 23 into Implement Detent 17 or Groove 18 (shown in FIGS. 14 and 15). FIG. 16 also shows locking ball hole seating diameter 24, which is slightly smaller than the locking ball diameter. Locking ball exposure depth 22 (slightly larger than engagement depth 23) is shown beyond tool socket locking ball hole 9a (shown in FIG. 11).

ASSEMBLY EXAMPLE

Referring generally to FIG. 11, in order from left to right, tool socket 9, having a length of about 1.1 inches, a locking ball hole 9a of about 0.188 inches diameter, and an outer diameter (OD) of about 0.79 inches, an inner diameter (ID) of about 0.63 inches by 0.8 inches deep interval for ½ inch-20 THD NFT is inserted into locking collar 1. Locking spring 7, having a non-compressed coiled length of about 0.8 inches, is placed over the end of tool socket 9 and then the threaded portion of tool socket 9 is threaded onto the receiving end of articulating clevis 2, also having ½ inch-20 THD NFT threads. Locking collar 1 is about 0.85 inches long, having OD of about 1.02 inches, ID of about 0.8 inches. Articulating clevis 2 is about 1.775 inches long, not including the combined extended and threaded portion 2a (FIGS. 9A and 9B) having a length of about 0.2 inches, Excluding the combined extended and threaded portion, the distance to the open channel portion 2b is about 1.25 inches and the distance to the pivot screw or cable stay receiving hole 2c is about 0.75 inches. The open channel end of the articulating clevis is placed into the chassis base 3 in a perpendicular direction, such that the open channel 2b of the articulating clevis 2 lines up with the open channel portion 3b of the chassis base 3 (FIGS. 10A and 10B). Lead screw nut 6, having a length of about 1 inch, OD of about 0.5 inches (it is a solid metal cylinder in this example, thus not having an ID), and a lead screw nut hole 6a (FIGS. 1, 2, 11) in the center perpendicular to the cylinder length, is placed through the chassis base open portion 3b and the articulating clevis open portion 2b. The lead screw nut 6 is affixed to the articulating clevis and chassis by means of a lead screw 11 (FIGS. 1, 2) passing and threading into lead screw nut hole 6a, such that turning the lead screw 11 by means of the lead screw cap ball 5 causes the articulating clevis 2 to be change angle perpendicular to the chassis base 3. Chassis base 3 is about 1.6 inches long by about 1.4 inches wide, with an additional extended portion length of about 0.65 inches, the extended portion including ½ inch-20 THD NET threads. The distance from the extended portion comprising the threads to the chassis base open portion is about 0.65 inches and the distance from the extended portion comprising the threads to the pivot screw or cable stay receiving hole 3c (FIGS. 10A, 10B) is about 1.45 inches.

The entire assembly can then be completed by adding a lead screw cap ball 5 (FIGS. 1, 2) and/or by adding a cable stay 13 (FIGS. 3, 4). Finally, a tool or implement 20 (FIGS. 14, 15) can be inserted by the tool or implement end or shank 19 into the locking collar 1, such that the locking ball 8 (FIGS. 3, 16) engages at least one detent 17 thereby locking the tool axially and radially) or groove 18 (locking the tool at least radially) (FIGS. 14, 15).

TABLE 1

Listing of Figure Label Items

| Label | Description |
|---|---|
| 1 | Locking Collar |
| 1a | Locking Collar Locating Indent |
| 1b | Locking Ball Groove |
| 2 | Articulating Clevis |
| 2a | Threaded Portion of Articulating Clevis |
| 2b | Open Channel Portion of Articulating Clevis |
| 2c | Pivot Screw or Cable Stay Receiving Hole on Articulating Clevis |
| 3 | Chassis Base for lead screw assembly, pivot screw and articulating clevis |
| 3a | Threaded portion of chassis base |
| 3b | Open Channel Portion of Chassis Base |
| 3c | Pivot Screw or Cable Stay Receiving Hole on Chassis Base |
| 3d | Lead Screw Receiving Hole |
| 4 | Pivot Screw (can be removed and replaced with cable stay attachment (13)) |
| 5 | Lead Screw Cap Ball |
| 6 | Lead Screw Nut |
| 6a | Lead Screw Nut Hole |
| 7 | Locking Spring |
| 8 | Locking Ball |
| 9 | Tool Socket (threads onto articulating clevis) |
| 9a | Locking Ball Hole on Tool Socket |
| 10 | Lead Screw End (Capscrew) |
| 11 | Lead Screw |
| 12 | Exit Angle in Locking Collar for Locking Ball |
| 13 | Cable Stay Attachment |
| 13a | Cable Stay Attachment Ring |
| 14 | Straight Section in Locking Collar for Locking Ball |
| 15 | Angled Section Length in Locking Collar for Locking Ball |
| 16 | Tool or Implement end |
| 17 | Detent(s) |
| 18 | Groove |
| 19 | Tool or Implement end or shank inserted into Locking Collar |
| 20 | Tool or Implement Coupling Part (overall) |
| 21 | Locking Ball Hole Diameter |
| 22 | Locking Ball Exposure Depth beyond Tool Socket Locking Ball Hole 9a |
| 23 | Locking Ball Engagement Depth into Implement Detent 17 or Groove 18 |
| 24 | Locking Ball Hole Seating Diameter |

There are, of course, a range of sizes and relative dimensions which one may employ in the practice of this invention and practitioners of these relevant arts, having learned of this disclosure, may devise embodiments other than those specifically described or referred to in this disclosure without departing from the concepts proscribed by the claims which follow.

What is claimed is:

1. A terminal device for releasable attachment to the distal end of an arm prosthesis and providing means for coupling with an implement in a variety of positions relative to the arm prosthesis, said terminal device comprising a structure having a proximate end chassis base and an distal end locking ring collar, said chassis base attached to the distal end of the prosthesis, and said locking ring collar being operably affixed onto an articulating clevis pivotably and perpendicularly mated into a slotted opening traversing the chassis base, the distal end of the locking ring collar having a hollow end for releasable insertion therein of an implement by means of an implement coupling part comprising a locking ring collar mechanism, wherein the locking ring collar mechanism comprises a locking ring collar, a locking ball, a locking spring, and a tool socket, wherein the locking ring collar comprises a visual locking ball locating indent, a locking ball groove comprising an angled section length and a straight section length, the angled section length located on the locking ring collar implement connecting end and comprising at least about 10% of the straight section length, the locking ball groove in close proximity to the visual locking ball locating indent;

a locking ball constrained within a locking ball hole in the tool socket and in communication with the locking ball groove;

wherein the tool socket comprising the locking ball is concentrically surrounded by the locking spring, which locking spring is in turn concentrically surrounded by the locking ring collar, wherein the pivotable means is provided by a lead screw mounted within, and traversing, the chassis base in a direction parallel to the fore-aft axial alignment thereof, and mounted within, and traversing, the articulating clevis in a direction normal to the distal-proximate axial alignment thereof, said lead screw communicating with lead screw nut of said articulating clevis, said lead screw being revolvable by means visibly mounted at one end of said lead screw.

2. The terminal device of claim 1 wherein the angled section length has an angle greater than 5 degrees and as high as 50 degrees.

3. The terminal device of claim 1 wherein the chassis base has a threaded extension on its proximal end for threading into an annular threaded receptacle adapter of matching size and threads, said receptacle being at the distal end of an arm prosthesis.

4. The terminal device of claim 1 wherein a cable stay attachment is attached to the articulating clevis and into the chassis base.

5. The terminal device of claim 1 wherein the implement coupling part comprises a circular bar of a dimension to fit closely within the hollow portion of the distal end of the locking ring collar, said implement coupling part having at least one securing detent and/or a securing groove operable at its outer surface which cooperates in releasable connection with a locking ball within said hollow portion when the implement coupling part is inserted into said hollow portion.

6. The terminal device of claim 1 wherein the implement held by the implement coupling part is selected from groups consisting of cutting tools, wrenches, clamping tools, screw drivers, hammers, scrapers, brushes, pencils, awls, scoops, planes, fishing rods, and stirring devices.

7. The terminal device of claim 1 wherein the articulating clevis and the chassis base are constructed of aircraft aluminum alloy.

8. The terminal device of claim 1 wherein the angled section length located on the locking ring implement connecting end has an angle greater than 10 degrees and up to 50 degrees.

9. The terminal device of claim 1 wherein the angled section length located on the locking ring collar implement connecting end comprises from at least about 10% of the straight section length to 100% of the straight section length.

10. The terminal device of claim 1 further comprising a tool or implement radially and axially attached to the locking ring collar by means of at least one detent.

* * * * *